(12) United States Patent
Wong et al.

(10) Patent No.: US 9,770,490 B2
(45) Date of Patent: Sep. 26, 2017

(54) ORAL DELIVERY FOR HEMOGLOBIN BASED OXYGEN CARRIERS

(71) Applicant: Billion King International Ltd., Hong Kong (HK)

(72) Inventors: Bing Lou Wong, Irvine, CA (US); Sui Yi Kwok, Hong Kong (HK)

(73) Assignee: Billion King International Ltd., Hong Kong (HK)

( * ) Notice: Subject to any disclaimer, the term of this patent is extended or adjusted under 35 U.S.C. 154(b) by 68 days.

(21) Appl. No.: 14/754,668

(22) Filed: Jun. 29, 2015

(65) Prior Publication Data
US 2015/0313968 A1 Nov. 5, 2015

Related U.S. Application Data

(62) Division of application No. 13/592,398, filed on Aug. 23, 2012, now Pat. No. 9,066,933.

(51) Int. Cl.
| | | |
|---|---|---|
| *A61K 38/42* | (2006.01) | |
| *A61K 9/28* | (2006.01) | |
| *A61K 9/20* | (2006.01) | |
| *A61K 9/48* | (2006.01) | |
| *A61K 9/00* | (2006.01) | |
| *A61K 9/19* | (2006.01) | |
| *A61K 9/51* | (2006.01) | |
| *B82Y 5/00* | (2011.01) | |

(52) U.S. Cl.
CPC ............ *A61K 38/42* (2013.01); *A61K 9/0095* (2013.01); *A61K 9/19* (2013.01); *A61K 9/2095* (2013.01); *A61K 9/2846* (2013.01); *A61K 9/2866* (2013.01); *A61K 9/2893* (2013.01); *A61K 9/4833* (2013.01); *A61K 9/4891* (2013.01); *A61K 9/5138* (2013.01); *A61K 9/5146* (2013.01); *A61K 9/5161* (2013.01); *B82Y 5/00* (2013.01)

(58) Field of Classification Search
None
See application file for complete search history.

(56) References Cited

U.S. PATENT DOCUMENTS

| | | |
|---|---|---|
| 6,399,116 B1 | 6/2002 | Xiu |
| 6,620,788 B1 * | 9/2003 | Tanida ............... A61K 9/0095 424/463 |
| 7,932,356 B1 | 4/2011 | Wong et al. |
| 7,989,593 B1 | 8/2011 | Wong et al. |
| 8,048,856 B1 | 11/2011 | Wong et al. |
| 8,084,581 B1 | 12/2011 | Wong et al. |
| 8,106,011 B1 | 1/2012 | Wong et al. |
| 2009/0117207 A1 * | 5/2009 | Zoltani ............... A61K 31/138 424/699 |

OTHER PUBLICATIONS

Labrude (Experientia (Feb. 9, 1981) 37:1020-1021).*
Fitzgerald et al., Medical Journal of Australia, MJA (May 2011) 194(9), 471-473.*
Carpenter et al., Rationale design of stable lyophilized protein formulations: theory and practice, in "Rationale Design of stable protein formulations-theory and practice" (J.F. Carpenter and M.C. Manning eds.) (2002) Kluwer Academic/Plenum publishers, New York, pp. 109-133.*
Artursson, P., et al. "Effect of chitosan on the permeability of monolayers of intestinal epithelial cells (Caco-2)." Pharm Res., 1994, 11: 1358-1361.
Ballard, T.S., et al. "Regulation of tight-junction permeability during nutrient absorption across the intestinal epithelium." Annu. Rev. Nutr, 1995, 15: 35-55.
Barnikol, W.K., et al. "Complete healing of chronic wounds of a lower leg with haemoglobin spray and regeneration of an accompanying severe dermatoliposclerosis with intermittent normobaric oxygen inhalation (INBOI): a case report." Ger Med Sci., 2011, 9 (DOI: 10.3205/000131).
Barrett, K.E., et al. "New Delhi: Tata-McGraw-Hill." Ganong's Review of Medical Physiology, 2009, 23rd edition, pp. 619-20.
Bonaventura, C., et al. "Allosteric effects on oxidative and nitrosative reactions of cell-free hemoglobin." IUBMB Life, 2007, 59(8-9): 498-505.
Brunel, F., et al. "Self-assemblies on chitosan nanohydrogels." Macromol Biosci., 2010, 10(4): 424-432.
Cicco, G., et al. "Wound healing in diabetes: hemorheological and microcirculatory aspects." Adv Exp Med Biol. 2011, 701: 263-269.
Dünnhaupt, et al. "Distribution of thiolated mucoadhesive nanoparticles on intestinal mucosa." International Journal of Pharmaceutics, 2011, 408 (1-2): 191-199.
Hackett, P.H., et al. "Dexamethasone for prevention and treatment of acute mountain sickness." Aviat space Environ Med., 1988, 59: 950-954.
Hiromi, Sakai, et al. "Review of Hemoglobin-Vesicles as Artificial Oxygen Carriers." Artificial organs, 2009, 33(2): 139-145.
Iwasaki, N, et al. "Feasibility of polysaccharide hybrid materials for scaffolds in cartilage tissue engineering: evaluation of chondrocyte adhesion to polyion complex fibers prepared from alginate and chitosan." Biomacromolecules, 2004, 5 (3): 828-833.

(Continued)

*Primary Examiner* — Marcela M Cordero Garcia
*Assistant Examiner* — Catherine Mader
(74) *Attorney, Agent, or Firm* — Spruson & Ferguson HK (57) ABSTRACT

A process for making hemoglobin based oxygen carrier (HBOC) containing pharmaceutical composition suitable for oral delivery and the composition formed thereby are described. There are three exemplary composition configurations which include (1) hemoglobin-loaded nanoparticles solution, (2) enteric-coated hemoglobin capsules and (3) enteric-coated hemoglobin tablets. To facilitate the bioavailability and bio-compatibility of hemoglobin, intestinal absorption enhancers are added in each of the HBOC formulations. Protective layers ensure delivery of an intact hemoglobin structure in intestinal tract without degradation in the stomach. The HBOC formulations may be used for preventive or immediate treatment of high altitude syndrome (HAS) or for treatment of hypoxic conditions including blood loss, anemia, hypoxic cancerous tissue, and other oxygen-deprivation disorders. In addition to delivering oxygen, the heme group of hemoglobin from HBOC formulations can provide heme iron to the human body to aid in the production of more red blood cells.

24 Claims, 5 Drawing Sheets

(56) References Cited

OTHER PUBLICATIONS

Levien, L.J. "South Africa: clinical experience with Hemopure." ISBT Science Series, 2006, 1(1): 167-173.
Lin, Y.H., et al. "Multi-ion-crosslinked nanoparticles with pH-responsive characteristics for oral delivery of protein drugs." J Control Release., 2008: 132(2), 141-149.
Makhlof, A., et al. "Design and evaluation of novel pH-sensitive chitosan nanoparticles for oral insulin delivery." Eur J Pharm Sci., 2011, 42(5): 445-451.
Natanson, C., et al. "Cell-free hemoglobin-based blood substitutes and risk of myocardial infarction and death—A meta-analysis." J Amer. Med. Assoc., 2008, 299(19): 2304-2312.
Niederhofer, A., et al. "A method for direct preparation of chitosan with low molecular weight from fungi." Eur J Pharm Biopharm, 2004, 57: 101-105.
Paralikar, Swapnil J., et al. "High-altitude medicine." Indian J Occup Environ Med., 2010, 14(1): 6-12.
Remy, B., et al., "Red blood cell substitutes: fluorocarbon emulsions and hemoglobin emulsions." British Medical Bulletin, 1999, 55: 277-298.
Richard, A., et al. "Poly(glutamic acid) for biomedical applications." Crit Rev Biotechnol, 2001, 21: 219-232.
Sonaje, K., et al. "Enteric-coated capsules filled with freeze-dried chitosanlpoly(gamma-glutamic acid) nanoparticles for oral insulin delivery." Biomaterials, 2010, 31(12): 3384-3394.
Sudarshan, N., et al. "Antibacteri action of chitosn." Food Biotechnology, 1992, 6(3): 257-272.

\* cited by examiner

ORAL DELIVERY FOR HEMOGLOBIN BASED OXYGEN CARRIERS

COPYRIGHT NOTICE/PERMISSION

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. The following notice applies to the processes, experiments, and data as described below and in the drawings attached hereto: Copyright © 2012-15, Billion King International Limited, All Rights Reserved.

CROSS-REFERENCE TO RELATED APPLICATIONS

This application is a divisional application of the U.S. non-provisional patent application Ser. No. 13/592,398 filed Aug. 23, 2012 which claims priority from the U.S. provisional patent application Ser. No. 61/531,224 filed Sep. 6, 2011, and the disclosure of which are incorporated by reference in their entirety.

TECHNICAL FIELD

The present invention relates to a process for making hemoglobin based oxygen carrier (HBOC) containing pharmaceutical compositions suitable for oral delivery and the compositions produced thereby. The orally-deliverable HBOC compositions are suitable for treating a variety of conditions where enhanced tissue oxygenation is desirable.

BACKGROUND OF INVENTION

Hemoglobin plays an important role in most vertebrates for gaseous exchange between the vascular system and tissue. It is responsible for carrying oxygen from the respiratory system to the body cells via blood circulation and also carrying the metabolic waste product carbon dioxide away from body cells to the respiratory system, where the carbon dioxide is exhaled. Since hemoglobin has this oxygen transport feature, it can be used as a potent oxygen supplier if it can be stabilized ex vivo and used in vivo.

Development of hemoglobin based oxygen carriers (HBOCs) has been pursued as an alternative to treatment with whole blood products. Typically, past HBOCs have been used as resuscitative fluids for hemorrhagic shock in emergency situations. However, there are various complications that have prevented widespread use of HBOCs. Such complications include extravasation of small-sized hemoglobin, myocardial infarction, hypertension, and renal toxicity (Bonaventura et al., 2007; Natanson et al., 2008). Various attempts to stabilize and purify the hemoglobin in HBOCs have yielded promising results; however, there is still no FDA-approved HBOC for routine clinical use.

While substantial research has been devoted to HBOC formulations for intravenous delivery, such intravenous delivery can be inconvenient or impossible in non-hospital settings. Therefore, there is a need in the art for HBOC compositions that can be delivered orally in non-hospital settings. Such compositions can be used to treat conditions where enhanced tissue oxygenation is desirable either due to medical or environmental conditions.

One environment where enhanced oxygenation is desirable is at high altitudes. High altitude syndrome (HAS) typically appears on rapid ascent to an altitude above 2,500 meters. Every day thousands of people travel to high altitudes, such as mountainous regions, and about 20% of them experience symptoms of HAS including headache, nausea, dizziness and sleep difficulty. Normally, the symptoms are sufficiently mild that they can be relieved by limiting activity and remaining at the same altitude for a few days for acclimatization. Without proper acclimatization and continuing to ascend, the sickness may progress to high altitude cerebral edema or high altitude pulmonary edema which is life threatening conditions that need to be treated aggressively (Paralikar, 2010).

Lower oxygen levels at high altitude increases ventilation by stimulating peripheral chemoreceptors, leading to hyperventilation. Hyperventilation reduces the alveolar carbon dioxide level, resulting in hypocapnia and alkalosis of blood. At the same time, cerebral blood flow increases to ensure adequate oxygen delivery. The resultant change in blood pH and the increase of cerebral pressure cause the mild symptoms described above. In response to the hypoxic environment, the human body initiates a series of adaptive mechanisms, i.e. acclimatization. For instance, the kidney excretes excessive bicarbonate and conserves hydrogen ions. Finally, blood and cerebrospinal fluid pH as well as ventilation rate are restored. Another important regulation is that hypoxia stimulates the release of the hormone erythropoietin from the kidney. Erythropoietin-sensitive committed stem cells in the bone marrow are stimulated to differentiate into red blood cells (RBC). New RBC can be generated and circulated in the blood stream within 4-5 days (Barrett et al., 2009). Long-term acclimatization leads to an increase in blood volume and RBC cell mass, therefore the oxygen-carrying capacity can be increased. Blood alkalosis shifts the oxygen-hemoglobin dissociation curve to the left. Meanwhile, a concomitant increase in RBC 2,3-diphosphoglycerate shifts the curve to the right. As a result, a net increase in p50 (affinity between hemoglobin and oxygen decreases) increases $O_2$ available to tissues (Barrett et al., 2009).

There have been various approaches taken in the past to treat HAS. Treatment with acetazolamide increases the rate of acclimatization (Paralikar, 2010). Acetazolamide, a renal carbonic anhydrase inhibitor, reduces bicarbonate re-absorption to maintain the balance of hydrogen ions. Moreover, acetazolamide inhibits cerebrospinal fluid production and reduces cerebrospinal fluid pressure. Steroids, particularly dexamethasone, have also been found to be effective in relieving symptoms (Hackett et al., 1988). However, both drugs (acetazolamide and steroids) are not targeting at enhancing cellular oxygen delivery to alleviate the condition. Additionally there have been reports that the Chinese herbal medicine *Rhodiola* can enhance blood oxygen levels (Xiu, 2002). However, there are side effects to *Rhodiola* including irritability, restlessness, and insomnia.

Regarding HBOCs, there have been some attempts to create alternative delivery mechanisms for the hemoglobin. One approach formulates hemoglobin-vesicles that mimic the cellular structure of RBC. Hemoglobin-vesicles are formed by encapsulating hemoglobin within a thin lipid bilayer membrane. However, such formulations, as with prior art HBOCs, are designed for intravenous delivery.

Oral drug delivery is convenient for patients, particularly in non-clinical settings; however several potential problems need to be solved, especially for protein-based drugs such as HBOCs. First, peptides or proteins can be degraded and digested by low pH gastric medium in the stomach and proteases in pancreatic juice. Second, the absorption of peptides or proteins in the intestine is hindered by their high molecular weight and hydrophilicity. Thus there is a need in the art for oral delivery HBOC compositions to ensure safe and effective delivery of oxygen to patients having a need for enhanced oxygen transport. Such a composition could be used to treat patients having HAS or other hypoxic conditions including blood loss, anemia, hypoxic cancerous tissue, and other oxygen-deprivation-based disorders.

SUMMARY OF INVENTION

The present invention relates to processes for making hemoglobin based oxygen carrier (HBOC) containing pharmaceutical compositions suitable for oral delivery and to the hemoglobin based oxygen carriers produced thereby. The formulations of the invention have particular application for preventive or immediate treatment of high altitude syndrome (HAS) by oxygen delivery; however, the oral formulations of the present invention can be used in any situation where it is desirable to enhance oxygen delivery to tissue with a HBOC such as for treatment of hypoxic conditions including blood loss, anemia, hypoxic cancerous tissue, and other oxygen-deprivation disorders.

The present HBOC formulations use hemoglobin-loaded nanoparticles capsules or tablets to facilitate the bioavailability and bio-compatibility of the hemoglobin. Protective layers in different configurations assure intact structure of hemoglobin, without degradation in stomach. Optional additional excipients can be added for time-release or controlled-release compositions or for composition preservation and/or stabilization.

In one embodiment a hemoglobin-based oxygen carrier is orally delivered to a subject in need thereof by providing at least one of the following delivery systems containing the hemoglobin based oxygen carrier: a nanoparticle solution, an enteric-coated capsule, and/or an enteric-coated tablet. The delivery system is configured such that the hemoglobin based oxygen carrier is released in the intestinal tract such that the hemoglobin is delivered to a patient bloodstream in a substantially undegraded form. As used herein, the term "substantially undegraded form" means that at least 90% of the hemoglobin molecules retain the structure of comparable native hemoglobin.

DETAILED DESCRIPTION OF INVENTION

The present invention is directed to oral delivery formulations for HBOCs which deliver oxygen to the vasculature via oral administration. Three different categories of HBOCs for oral administration are described. Hemoglobin loads differently in each composition to create individualized and specific releasing and absorbing properties of the HBOC. In the compositions according to the present invention, the hemoglobin proteins are encapsulated in an acid-resistant material to avoid acid degradation in the stomach and enable absorption in the intestinal tract of a subject being administered with the compositions. The three pharmaceutical configurations are: (1) hemoglobin-loaded nanoparticles solution, (2) enteric-coated hemoglobin capsules and (3) enteric-coated hemoglobin tablets. A variety of hemoglobin is used in the pharmaceutical compositions including purified hemoglobin, cross-linked hemoglobin, non-polymeric tetrameric hemoglobin, polymeric hemoglobin, and conjugated hemoglobin of various molecular weights. Examples of hemoglobin that can be used in the oral pharmaceutical compositions of the present invention are set forth in U.S. Pat. Nos. 7,932,356, 7,989,593, 8,048,856, 8,084,581, 8,106,011, the disclosures of which are incorporated by reference herein.

In the hemoglobin-loaded nanoparticle solution, hemoglobin is embedded within a polyelectrolyte complex, comprised of anionic polymer and cationic chitosan chains to ensure the intact structure of hemoglobin and enabling efficient absorption via the oral administration route. Anionic polymers that could complex with chitosan include poly(methacrylic acid)-poly(methyl methacrylate) (PMAA-PMMA) copolymer, hydroxyl propylmethylcellulose phthalate (HPMCP) and gamma-glutamic acid ($\gamma$-PGA). The proportion of anionic and cationic components are maintained at ratio at which positively charged nanoparticles are produced, which is found to have enhanced mucosal adhesion to the negatively charged intestinal epithelial (Dünnhaupt et al., 2011).

Chitosan, a cationic polysaccharide, is derived from chitin by alkaline deacetylation. The polysaccharide chain is constituted by N-glucosamine and N-acetyl glucosamine units. Chitosan is non-toxic and soft tissue compatible (Iwasaki et al., 2004). More importantly, chitosan has a special property of adhering to the mucosal surface and transiently opening the tight junctions between epithelial cells (Artursson et al., 1994), making it an ideal intestinal absorption enhancer.

Figure 1:
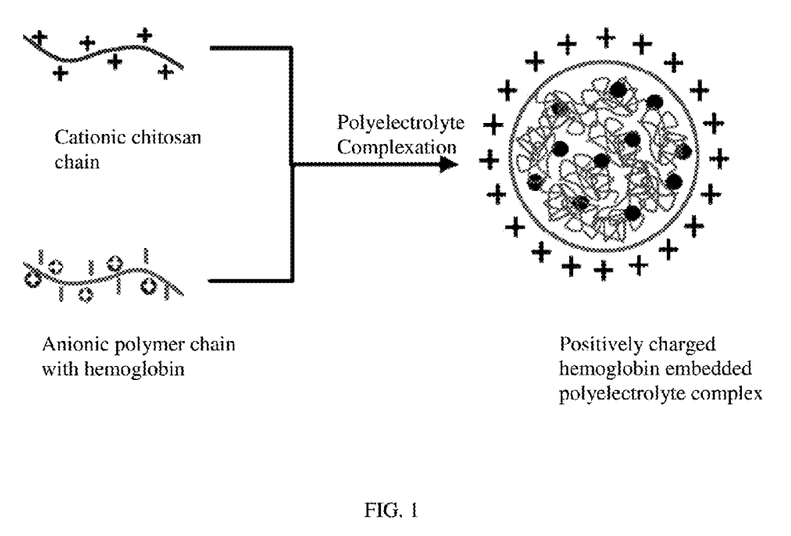
FIG. 1 shows the formation and structure of a hemoglobin loaded nanoparticle.

Hemoglobin-loaded nanoparticles are produced via polyelectrolyte complexation under an aqueous-based condition at room temperature without using harmful organic solvents that would disrupt the intact structure of hemoglobin. The nanoparticles include three major components: anionic polymer, chitosan, and hemoglobin. FIG. 1 illustrates the complexation process of the cationic chitosan chains, pre-mixed anionic polymer chains and hemoglobin, which thereby producing the final product of a positively charged hemoglobin-loaded nanoparticle. The pre-mixed solution of anionic polymer and hemoglobin is adjusted to a final pH that is above the isoelectric point of hemoglobin, inducing a positive charge on the protein surface, hence a strong affinity with the anionic polymer. Exemplary methods for forming the nanoparticles are disclosed in Makholf et al., 2011, Sonaje et al., 2010, Lin et al., 2008, Brunel et al., 2010, the disclosures of which are incorporated by reference.

It has been demonstrated that chitosan exhibit antibacterial activity against *Escherichia coli*, and therefore no preservative is needed for long term storage (Sudarshan et al., 1992). However, to prolong shelf-life of the pharmaceutical compositions, vitamin C or N-acetyl cysteine (NAC) is optionally added to the nanoparticle mixture. Vitamin C or N-acetyl cysteine acts as antioxidant to prevent the formation of inactive met-hemoglobin which cannot deliver oxygen. Inactive ingredients (excipients) optionally include coloring, flavoring, desiccants, further coatings for facilitating swallowing of the oral compositions, etc.

Figure 4:
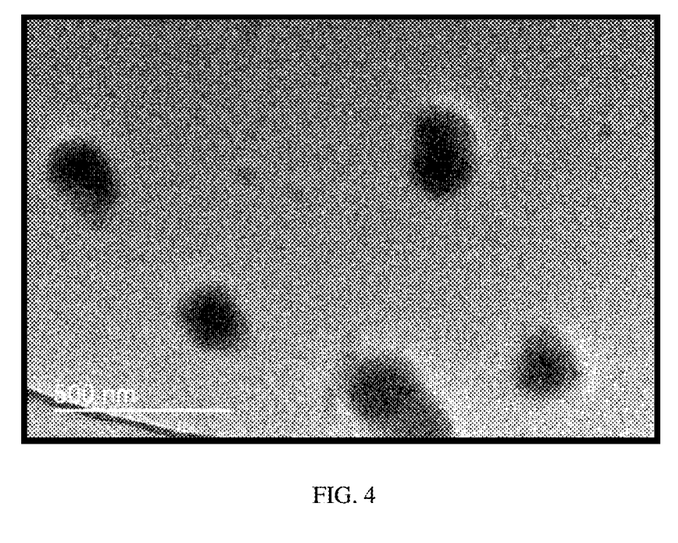
FIG. 4 shows the transmission electron microscope image of hemoglobin loaded nanoparticles.

In one embodiment, 50 mL of 0.05% w/v PMAA-PMMA copolymer aqueous solution is prepared and adjusted to pH 7. Hemoglobin (200 mg) is added to the prepared PMAA-PMMA copolymer solution and mixed well to form a first mixture. Same volume (50 mL) of 0.05% w/v chitosan (molecular weight: 130 k) aqueous solution is prepared and adjusted to pH 4.5. The first mixture is then added dropwise to the pH-adjusted chitosan solution under magnetic stirring at room temperature. Nanoparticles are collected by ultracentrifugation at 20,000 rpm for 1 hour. The pellet containing a plurality of nanoparticles after ultracentrifugation is re-suspended in 5 mL of deionized water for further characterization. Particle size and zeta potential are measured using dynamic light scattering and laser Doppler electrophoresis (Zetasizer HS3000, Malvern), the results of which are presented in Table 1. Highly positively charged (41 mV) hemoglobin-loaded nanoparticles with a particle size of about 574 nm is produced. Loading of hemoglobin into the polyelectrolyte complex increases both the particle size and zeta potential compared to the blank nanoparticles prepared by the same procedures. Spherical morphology of hemoglobin-loaded nanoparticles are also shown in FIG. 4 obtained by the transmission electron microscope (JEM-2011, JEOL). The encapsulation/association efficiency percentage (AE %) and final product concentration are presented in Table 1. The quantity of hemoglobin is measured and determined by a HPLC-UV system (Waters 1525, Waters) at a wavelength of about 410 nm. The column used is a silica-based gel filtration column (BioSep-SEC-S 2000 SEC, 300×7.8 mm, Phenomenex). Flow rate and injection volume are 25 mL/min and 30 µL respectively. AE % is calculated by the following equation:

$$AE\% = \frac{\text{total amount of hemoglobin} - \text{free hemoglobin in supernatant}}{\text{total amount of hemoglobin}} \times 100$$

Lyophilization is a well-established technique to create stabilized dry protein formulations. The method of the present invention describes hemoglobin formulations prepared by lyophilization with the addition of cryoprotectants and intestinal absorption enhancers before fabricating into enteric-coated capsules or tablets. Cryoprotectants such as glucose, sucrose or trehalose are added to the hemoglobin solution to preserve the structure of protein during lyophilization. Intestinal absorption enhancers such as polyoxyethylene-20-sorbitan monooleate, poly(ethylene oxide)-poly(propylene oxide)-poly(ethylene oxide) tri-block copolymer, cyclodextrin, oleic acid, sodium decanoate, sodium octanoate, sodium deoxycholate and sodium cholate hydrate are included in the lyophilization formulations. Other stabilizers for the hemoglobin may also be included such as antioxidant.

In an embodiment, six lyophilization formulations (Table 2) are tested using a laboratory freeze dryer (LYOBETA 25, Telstar) under operating parameters listed in Table 3. Sucrose is added as a cryoprotectant and N-acetyl cysteine as an antioxidant. Two non-ionic surfactants are added to the hemoglobin solution as a stabilizer and intestinal absorption enhancer. Both polyoxyethylene-20-sorbitan monooleate (commonly known as Polysorbate 80) and poly(ethylene oxide)-poly(propylene oxide)-poly(ethylene oxide) tri-block copolymer (commonly known as Polyethylene-polypropylene glycol, PPG) are FDA approved excipients for oral formulations. PPG is a triblock copolymer with a PEO-PPO-PEO weight ratio of 40%-20%-40% and a molecular weight of 8,400 Da. Met-hemoglobin level is measured before and after lyophilization. The lyophilized samples are reconstituted in dionised water before met-hemoglobin measurement using a blood gas analyzer (IL 682 Co-Oximeter System, Instrumental Laboratory). There is no significant change in met-hemoglobin level after lyophilization. The group with PPG (Formulation Samples F3, F6; shown in Table 3) has the lowest met-hemoglobin level compared to the other formulations without PPG.

TABLE 1

| Sample | Particle Size [nm] | Zeta Potential [mV] | Encapsulation/ Association Efficiency [%] | Product Hemoglobin Concentration [mg/mL] |
|---|---|---|---|---|
| Blank nanoparticle | 369 | 28 | — | — |
| Hemoglobin-loaded nanoparticle | 574 | 41 | 28.7 | 7.8 |

TABLE 2

| Step | Process | Temp [° C.] | Vacuum [mbar] | Time [hr] |
|---|---|---|---|---|
| 1 | Freezing | −60 | — | 2 |
| 2 | Freezing | −60 | — | 6 |
| 3 | Chamber Vacuum | −60 | 0.5 | 2 |
| 4 | Primary drying | −10 | 0.5 | 2 |
| 5 | Primary drying | −10 | 0.5 | 10 |
| 6 | Primary drying | 0 | 0.5 | 1 |
| 7 | Primary drying | 0 | 0.5 | 8 |
| 8 | Secondary drying | 15 | 0.2 | 1.5 |
| 9 | Secondary drying | 15 | 0.08 | 8 |
| 10 | Secondary drying | 25 | 0.08 | 1 |
| 11 | Secondary drying | 25 | 0.001 | 6 |

TABLE 3

| Sample | Hemoglobin [mg/mL] | Sucrose [M] | NAC [w/v %] | Polysorbate 80 [mM] | PPG [w/v %] | Met-Hb [%] before lyophilization | Met-Hb [%] After lyophilization |
|---|---|---|---|---|---|---|---|
| F1 | 5 | 0.25 | 0 | 0 | 0 | 6.3 | 6.9 |
| F2 | 5 | 0.25 | 0 | 3 | 0 | 6.3 | 7.7 |
| F3 | 5 | 0.25 | 0 | 0 | 0.2 | 6.3 | 6.5 |

TABLE 3-continued

| Sample | Hemoglobin [mg/mL] | Sucrose [M] | NAC [w/v %] | Polysorbate 80 [mM] | PPG [w/v %] | Met-Hb [%] before lyophilization | Met-Hb [%] After lyophilization |
|---|---|---|---|---|---|---|---|
| F4 | 5 | 0.25 | 0.2 | 0 | 0 | 6.3 | 7.0 |
| F5 | 5 | 0.25 | 0.2 | 3 | 0 | 6.3 | 7.2 |
| F6 | 5 | 0.25 | 0.2 | 0 | 0.2 | 6.3 | 6.5 |

To investigate the trans-epithelial transport of the lyophilized hemoglobin (Formulation Samples F1-F3; shown in Table 3), in vitro, Caco-2 cell monolayers on transwell setup is used. Caco-2 cell culture model, which is culture of the human epithelial colorectal adenocarcinoma cell line, is a well-recognized method to the study of human intestine function and thereby drug intestinal absorption mechanism. Firstly, Caco-2 cells are grown in the T75 flask. DMEM (high glucose, Gibco) supplemented with 10% Fetal bovine serum (FBS), 1% Non-essential amino acids (NEAA), and antibiotics (50 U/ml penicillin and 50 μg/ml streptomycin) is used as the culture medium. The grown Caco-2 cells are trypsinized and $6\times10^5$ cells are seeded onto each well of the tissue-culture treated polycarbonate Costar Transwell 6 wells/plates (growth area 4.7 $cm^2$, Corning Costar Corp., NY). The Caco-2 monolayer culture was kept in an atmosphere of 95% air and 5% $CO_2$ at 37° C. The medium is replaced every other day in the both apical and basolateral compartments. Millicell-Electrical Resistance System (Millipore Corp.) connected to a pair of chopstick electrodes is used to monitor the transepithelial electric resistance (TEER) which reveals the tightness of the tight junction between cells. The Caco-2 monolayer culture is used for the trans-epithelial transport study after 19-21 days after seeding. The difference in TEER between the blank and the cell monolayer should be in the range of 400 ohm/$cm^2$ to 500 ohm/$cm^2$. The cells are fed with fresh medium 24 hours prior to the trans-epithelial transport study. Before the start of the experiment, the cell monolayers are washed and incubated with pre-warmed Hank's balanced salt solution (HBSS), supplemented with $NaHCO_3$ (0.35 g/L) and 25 mM HEPES (if pH 6.5) or 10 mM methanesulfonic acid (if pH<6), for 30 min. HBSS are aspirated and refilled 1.5 ml HBSS to apical compartment and 2 ml to basolateral compartment. HBOCs and excipients are loaded into the apical compartment. FITC-dextran (4 kDa, Sigma) could be used as a positive maker to test the permeability of the cell monolayer. The initial TEER values were measured by Millicell-ERS. The cells are incubated at 37° C. with orbital shaking at 50 r.p.m. for 3 hours. TEER values are recorded at the time point of 1.5 and 3 hours. At the end of the experiment, 2 ml of HBSS at the basolateral compartment are collected and analyzed with high-performance liquid chromatography (HPLC) to quantify the pass-through HBOC. FITC-dextran is quantified using fluorescence spectrometer (EUROStar). Hemoglobin absorption percentage and the change in TEER at the end of the experiment are presented in Table 4. Absorption percentage is calculated as the amount of hemoglobin in the basolateral compartment at the end of the study compared to the initially loaded hemoglobin amount in the apical compartment. A 3.9-fold and 2.6-fold increase in hemoglobin absorption is induced by the addition of Polysorbate 80 and PPG respectively. The presence of Polysorbate 80 in sample F2 induces a more significant drop (10%) of TEER compared to sample F1, whereas there is no significant change in TEER for sample F3.

TABLE 4

| Samples | Absorption % | % of initial TEER |
|---|---|---|
| FITC-dextran | 5.6 | 91.8 |
| F1 (hemoglobin 10 mg) | 1.7 | 87.0 |
| F2 (hemoglobin 10 mg + Polysorbate 80 3 mM) | 6.6 | 76.8 |
| F3 (hemoglobin 10 mg + PPG 0.2%) | 4.4 | 97.1 |

Figure 2:
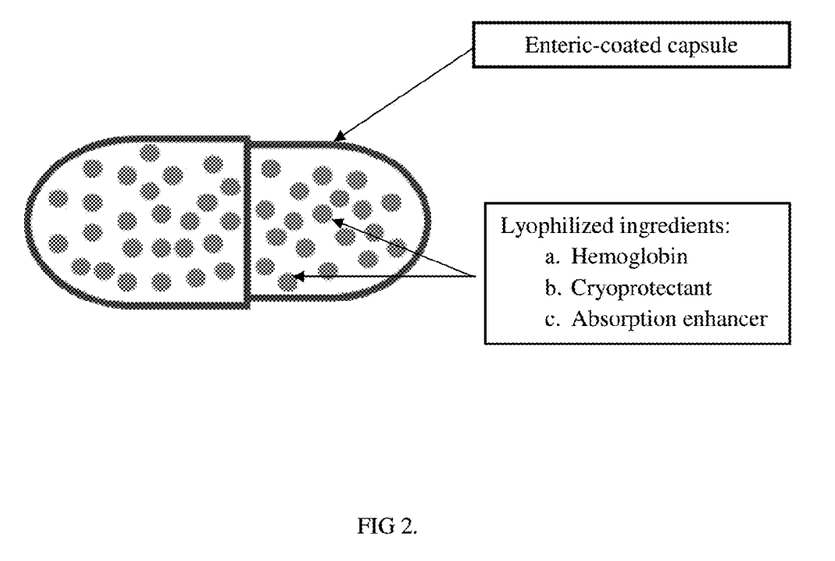
FIG. 2 shows the structure of enteric-coated hemoglobin capsule.
Figure 5:
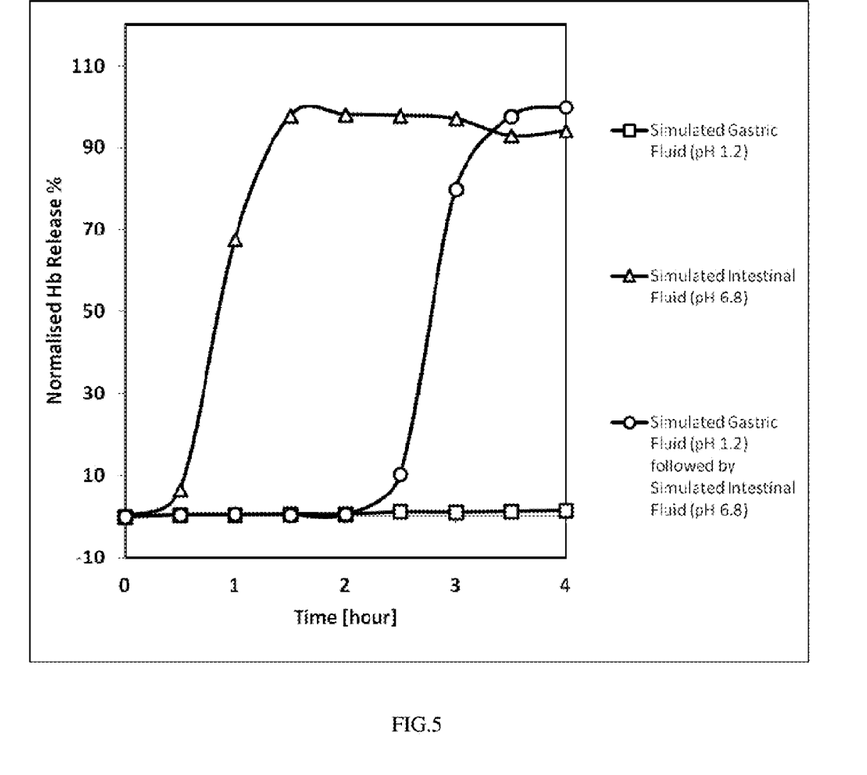
FIG. 5 shows the dissolution profiles of enteric-coated hemoglobin capsules in (1) simulated gastric fluids, (2) simulated intestinal fluid and also (3) simulated gastric fluid and simulated intestinal fluid in sequence.

In one embodiment, lyophilized hemoglobin solid mixture is encapsulated in enteric-coated capsules. Enteric-coated capsules are commercially available and are composed of gelatin with a polyacrylic resin coating. Enteric-coated capsule is acid-resistant but dissolves at pH levels of the order of 6-7 which is the pH level found in the intestines. FIG. 2 is a schematic diagram showing the basic structure of the enteric-coated capsule of the present invention. Release study of enteric-coated hemoglobin capsules is performed in simulated gastric fluid (pH 1.2, without pepsin) and simulated intestinal fluid (pH 6.8, without pancreatin) at 37° C. Three enteric-coated capsules (size 9) are each filled with 10 mg of lyophilized hemoglobin solid mixture. Each capsule is placed into 10 mL of release medium in three scenarios: (1) simulated gastric fluid for 4 hours; (2) simulated intestinal fluid for 4 hours; (3) simulated gastric fluid for 2 hours followed by simulated intestinal fluid for 2 hours. Amount of hemoglobin released at different sampling time is determined by HPLC-UV measurement at 410 nm. The dissolution profiles of the three scenarios are shown in FIG. 5. Hemoglobin is well-protected by the enteric-coated capsule in simulated gastric fluid and no hemoglobin is released in scenario 1. Hemoglobin is only released when placed in the simulated intestinal fluid in scenario 2 and 3.

In one embodiment, an in vivo study of freeze-dried hemoglobin is performed to evaluate the efficacy of systemic delivery of hemoglobin. Sprague Dawley (SD) rats (about 300 g, n=3) are subjected to oral administration of freeze-dried hemoglobin encapsulated in enteric coated capsule containing 9 mg of powder. Capsules are given to each rat with a feeding tube at a dose of 0.9 g/kg. Blood is collected from the tail vein to determine the plasma hemoglobin concentration using a hemoglobin analyzer (HemoCue® Plasma/Low Hb System). Plasma hemoglobin concentrations are measured before feeding and at time intervals of 3 and 6 hours post-feeding. Baseline plasma hemoglobin concentration is 0.17 g/dL and progressive increases over the study period of 6 hours. Plasma hemoglobin concentrations are 0.28 g/dL and 0.34 g/dL at 3 and 6 hour interval respectively, which accounted for 63.5% and 97.1% increase compared to baseline.

In one embodiment, the efficacy of the treatment of anemia by oral delivery of hemoglobin is studied by a hemorrhagic anemia animal model. Male adult Wistar rats with a mean body weight of 200-250 g are used in the study. The hemorrhagic anemia model is established by 30% blood phlebotomy, in which 15% of blood is removed on Day 1 followed by another 15% on Day 3. After each blood withdrawal, equal volume of saline solution is infused into the animal. Pressure is applied for hemostasis after wound closure, and antibiotics were given intramuscularly. Hemoglobin level is determined on Day 4 to confirm the establishment of the hemorrhagic anemia model (HGB<10 g/dL). The anemic rats are randomly divided into two groups, saline control group (n=6) and hemoglobin group (n=8). Lyophilized hemoglobin powder is reconstituted in saline solution to a concentration of 0.2 g/mL and is administered to the animal by oral gavage at a dose of 1 g/kg. The same volume (5 mL) of hemoglobin solution or saline solution is administrated to the animal orally twice a day, i.e. morning and evening with an interval of 8 hours. Blood parameters and body weight, including hemoglobin content (HGB, in Table 5), hematocrit (HCT, in Table 6), red blood cell count (RBC, in Table 7), mean corpuscular volume (MCV, in Table 8) and body weight (BW, in Table 9), are measured on day 7 and day 14 post-dosing. All data are presented as mean±standard deviation. T-TEST is used for statistical analysis. Values of $p<0.05$ are considered significant. It is found that there is a significant increase in HCT, RBC, MCV and BW on post-dose day 7 compared to the baseline value before blood withdrawal. Significant improvement in hemoglobin content (HGB), hematocrit (HCT), red blood cell count (RBC) and mean corpuscular volume (MCV) and maintaining body weight (BW) without adverse effect compared to the saline control group are also observed.

TABLE 5

Change in hemoglobin level (HGB, g/L)

| | Before Blood Withdrawal | After Blood Withdrawal | Post-dose Day 7 | Post-dose Day 14 |
| --- | --- | --- | --- | --- |
| Saline Group (Control) | 124.43 ± 7.43 | 75.29 ± 5.31[++] | 119.77 ± 7.76 | 119.57 ± 7.74 |
| Hemoglobin group | 128.13 ± 6.50 | 72.63 ± 4.04[++] | 135.5 ± 5.48** | 130.71 ± 8.80 |

[++]$p < 0.01$, compare with baseline value before blood withdrawal
**$p < 0.01$, compare with saline group value

TABLE 6

Change in hematocrit (%, HCT)

| | Before Blood Withdrawal | After Blood Withdrawal | Post-dose Day 7 | Post-dose Day 14 |
| --- | --- | --- | --- | --- |
| Saline Group (Control) | 38.91 ± 1.92 | 24.06 ± 1.55[++] | 34.91 ± 0.96[++] | 38.07 ± 1.96 |
| Hemoglobin Group | 37.49 ± 2.36 | 23.16 ± 1.27[++] | 39.81 ± 1.10[+],** | 40.31 ± 1.70[+] |

[+]$p < 0.05$,
[++]$p < 0.01$, compare with baseline value before blood withdrawal
**$P < 0.01$, compare with saline group

TABLE 7

Change in red blood cell count ($1 \times 10^{12}$/L, RBC)

| | Before Blood Withdrawal | After Blood Withdrawal | Post-dose Day 7 | Post-dose Day 14 |
| --- | --- | --- | --- | --- |
| Saline Group | 6.82 ± 0.33 | 4.03 ± 0.30[++] | 5.68 ± 0.14[++] | 5.95 ± 0.42[++] |
| Hemoglobin Group | 6.56 ± 0.42 | 3.85 ± 0.19[++] | 6.08 ± 0.45* | 6.12 ± 0.58 |

[++]$P < 0.01$, compare with baseline value before blood withdrawal
*$P < 0.05$, compare with saline group

TABLE 8

Change in mean corpuscular volume (fL, MCV)

| | Before Blood Withdrawal | After Blood Withdrawal | Post-dose Day 7 | Post-dose Day 14 |
| --- | --- | --- | --- | --- |
| Saline Group (Control) | 57.06 ± 1.07 | 59.76 ± 1.50[+] | 64.10 ± 1.14[++] | 64.10 ± 1.73[++] |

TABLE 8-continued

| Change in mean corpuscular volume (fL, MCV) | | | | |
|---|---|---|---|---|
| | Before Blood Withdrawal | After Blood Withdrawal | Post-dose Day 7 | Post-dose Day 14 |
| Hemoglobin Group | 57.15 ± 0.99 | 60.19 ± 0.97++ | 65.70 ± 1.12++,* | 66.40 ± 5.20++ |

++$P < 0.01$, compare with baseline value before blood withdrawal
*$P < 0.05$, compare with saline group

TABLE 9

| Change in rat body weight (g, BW) | | | | |
|---|---|---|---|---|
| | Before Blood Withdrawal | After Blood Withdrawal | Post-dose Day 7 | Post-dose Day 14 |
| Saline Group (Control) | 256.29 ± 4.46 | 240.86 ± 4.01++ | 244.71 ± 8.64+ | 254.71 ± 11.45 |
| Hemoglobin Group | 258.00 ± 8.87 | 255.75 ± 8.43** | 258.33 ± 9.03* | 260.25 ± 11.94 |

Figure 3:
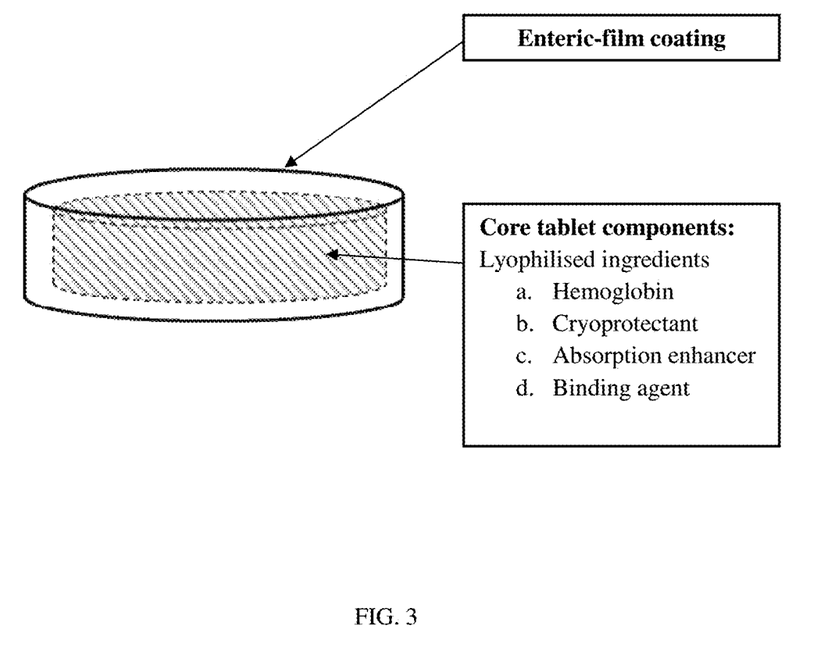
FIG. 3 shows the structure of enteric-coated hemoglobin tablet.

++$P < 0.01$, compare with baseline
*$P < 0.05$,
**$P < 0.01$ compare with saline group In another embodiment, lyophilized hemoglobin solid mixture is pressed into a core tablet, followed by an enteric film coating. The core tablet described herein uses lyophilized hemoglobin mixture as the active ingredient and other tablet forming excipients such as lactose monohydrate, polyvinylpyrrolidone, magnesium stearate, microcrystalline cellulose, anhydrous dibasic calcium phosphate. Optional excipients such as ethylcellulose, cellulose esters, poly (methacrylates) can be added to the lyophilized hemoglobin solid mixture to achieve a sustained release of hemoglobin and hence sustained delivery of oxygen to tissues. The thoroughly mixed powders are loaded to a tablet press machine, single-punch tablet press, or rotary tablet press to form the core tablet, which is then film coated by an enteric coating material, including poly(methacrylic acid)-poly (methyl methacrylate) copolymer, hydroxypropyl methylcellulose phthalate and cellulose acetate phthalate. FIG. 3 is a schematic diagram showing the basic structure of the enteric-coated tablet of the present invention. Compared to intravenous delivery of peptides or proteins, oral delivery has an advantage in pharmacokinetics because an oral delivery system enables controlled release of peptide or protein from the carriers. Such a controlled release mode of delivery of peptide or protein drug is unavailable in direct intravenous delivery. For hemoglobin being introduced into the vascular system, a controlled release and sustained elevation of the hemoglobin concentration in the blood has a greater physiological benefit than that from a sudden substantial increase of free hemoglobin in the injection site from direct injection. A rapid increase in the hemoglobin level increases the chance of developing side effects such as extravasation, myocardial infarction and renal toxicity.

The heme group of hemoglobin in HBOC consists of an iron (Fe) ion (charged atom) held in a heterocyclic ring. In addition to delivering oxygen to the human body by HBOC, the heme group can provide heme iron to the body to aid in the production of more red blood cells. Acetazolamide, steroids and *Rhodiola* cannot provide heme iron to the body.

Oral delivery of HBOCs is a non-invasive, convenient and efficient way to prevent or treat HAS, and therefore, it is favorable for people to take before or during travel from a sea level region to a high altitude region. Absorption of undegraded hemoglobin in intestinal tract, skipping de novo synthesis of hemoglobin, increases the oxygen-carrying capacity of blood thus increasing the rate of acclimatization. The orally-deliverable HBOCs can also be used to treat acute anemia due to blood loss or to prepare individuals for physically-demanding activities in normal or low oxygen supply atmosphere, e.g. for athletes, astronauts, divers, or navy personnel stationed in submarines. Improving tissue oxygenation by HBOCs is further useful for preventing/treating tissue ischemia, and promotes wound healing, such as diabetic foot ulcers. While the foregoing invention has been described with respect to various embodiments, such embodiments are not limiting. Numerous variations and modifications would be understood by those of ordinary skill in the art. Such variations and modifications are considered to be included within the scope of the following claims.

The following references relate to various aspects of the present invention and are incorporated by reference herein:

Artursson, P., et al. "Effect of chitosan on the permeability of monolayers of intestinal epithelial cells (Caco-2)." *Pharm Res.*, 1994, 11: 1358-1361.

Ballard, T. S., et al. "Regulation of tight-junction permeability during nutrient absorption across the intestinal epithelium." *Annu. Rev. Nutr*, 1995, 15: 35-55.

Barnikol, W. K., et al. "Complete healing of chronic wounds of a lower leg with haemoglobin spray and regeneration of an accompanying severe dermatoliposclerosis with intermittent normobaric oxygen inhalation (INBOI): a case report." *Ger Med Sci.*, 2011, 9 (DOI: 10.3205/000131).

Barrett, K. E., et al. "New Delhi: Tata-McGraw-Hill." *Ganong's Review of Medical Physiology*, 2009, 23rd edition, pp. 619-20.

Bonaventura, C., et al. "Allosteric effects on oxidative and nitrosative reactions of cell-free hemoglobin." *IUBMB Life*, 2007, 59(8-9): 498-505.

Brunel, F., et al. "Self-assemblies on chitosan nanohydrogels." *Macromol Biosci.*, 2010, 10(4): 424-432.

Cicco, G., et al. "Wound healing in diabetes: hemorheological and microcirculatory aspects." *Adv Exp Med Biol.* 2011, 701: 263-269.

Dünnhaupt, et al. "Distribution of thiolated mucoadhesive nanoparticles on intestinal mucosa." *International Journal of Pharmaceutics,* 2011, 408 (1-2): 191-199

Hackett, P. H., et al. "Dexamethasone for prevention and treatment of acute mountain sickness." *Aviat space Environ Med.,* 1988, 59: 950-954.

Hiromi, Sakai, et al. "Review of Hemoglobin-Vesicles as Artificial Oxygen Carriers." *Artificial organs,* 2009, 33(2): 139-145.

Iwasaki, N, et al. "Feasibility of polysaccharide hybrid materials for scaffolds in cartilage tissue engineering: evaluation of chondrocyte adhesion to polyion complex fibers prepared from alginate and chitosan." *Biomacromolecules,* 2004, 5(3): 828-833.

Levien, L. J. "South Africa: clinical experience with Hemopure." *ISBT Science Series,* 2006, 1(1): 167-173.

Lin, Y. H., et al. "Multi-ion-crosslinked nanoparticles with pH-responsive characteristics for oral delivery of protein drugs." *J Control Release.,* 2008: 132(2), 141-149.

Makhlof, A., et al. "Design and evaluation of novel pH-sensitive chitosan nanoparticles for oral insulin delivery." *Eur J Pharm Sci.,* 2011, 42(5): 445-451.

Natanson, C., et al. "Cell-free hemoglobin-based blood substitutes and risk of myocardial infarction and death—A meta-analysis." *J Amer. Med. Assoc.,* 2008, 299(19): 2304-2312.

Niederhofer, A., et al. "A method for direct preparation of chitosan with low molecular weight from fungi." *Eur J Pharm Biopharm,* 2004, 57: 101-105.

Paralikar, Swapnil J., et al. "High-altitude medicine." *Indian J Occup Environ Med.,* 2010, 14(1): 6-12.

Remy, B., et al., "Red blood cell substitutes: fluorocarbon emulsions and hemoglobin emulsions." *British Medical Bulletin,* 1999, 55: 277-298.

Richard, A., et al. "Poly(glutamic acid) for biomedical applications." *Crit Rev Biotechnol,* 2001, 21: 219-232.

Sonaje, K., et al. 'Enteric-coated capsules filled with freeze-dried chitosan/poly(gamma-glutamic acid) nanoparticles for oral insulin delivery." *Biomaterials,* 2010, 31(12): 3384-3394.

Sudarshan, N., et al. "Antibacteri action of chitosn." *Food Biotechnology,* 1992, 6(3): 257-272.

Wong, B. L., et al. (2011), U.S. Pat. Nos. 7,932,356, 7,989,593, 8,048,856 & 8,084,581

Wong, B. L., et al. (2012), U.S. Pat. No. 8,106,011

Xiu, R. (2002), U.S. Pat. No. 6,399,116

What is claimed is:

1. A method of preventing and/or treating high altitude syndrome (HAS) and/or hypoxic conditions comprising orally administering an enteric-coated capsule to a subject in need thereof, wherein said enteric-coated capsule is configured to deliver the hemoglobin-based oxygen carrier in a controlled release manner to a target site along the intestinal tract of the subject, wherein said delivering to the target site along the intestinal tract is pH-dependent, and wherein said enteric-coated capsule comprises a plurality of polyacrylic resin coated gelatin capsules filled with a lyophilized form of the hemoglobin based oxygen carrier a cryoprotectant, and one or more stabilizer and intestinal absorption enhancer, wherein said one or more stabilizer and intestinal absorption enhancer comprises at least a substance selected from the group consisting of polyoxyethylene-20-sorbitan monooleate and poly(ethylene oxide)-poly(propylene oxide)-poly(ethylene oxide) tri-block copolymer.

2. The method of claim 1, wherein said hemoglobin-based oxygen carrier comprises one or more of purified hemoglobin, cross-linked hemoglobin, non-polymeric tetrameric hemoglobin, polymeric hemoglobin, or conjugated hemoglobin.

3. A method of preventing and/or treating anemia and/or hypoxic conditions comprising orally administering an enteric-coated capsule to a subject in need thereof, wherein said enteric-coated capsule is configured to deliver the hemoglobin-based oxygen carrier in a controlled release manner to a target site along the intestinal tract of the subject, wherein said delivering to the target site along the intestinal tract is pH-dependent, and wherein said enteric-coated capsule comprises a plurality of polyacrylic resin coated gelatin capsules filled with a lyophilized form of the hemoglobin based oxygen carrier and a cryoprotectant, and one or more stabilizer and intestinal absorption enhancer, wherein said one or more stabilizer and intestinal absorption enhancer comprises at least a substance selected from the group consisting of polyoxyethylene-20-sorbitan monooleate and poly(ethylene oxide)-poly(propylene oxide)-poly(ethylene oxide) tri-block copolymer.

4. A method of preventing and/or treating high altitude syndrome (HAS) and/or hypoxic conditions comprising orally administering an enteric-coated tablet to a subject in need thereof, wherein said enteric-coated tablet is configured to deliver the hemoglobin-based oxygen carrier in a controlled release manner to a target site along the intestinal tract of the subject, wherein said delivering to the target site along the intestinal tract is pH-dependent, and wherein said enteric-coated tablet comprises a lyophilized form of the hemoglobin based oxygen carrier a cryoprotectant, a tablet forming excipient, and one or more stabilizer and intestinal absorption enhancer, wherein said one or more stabilizer and intestinal absorption enhancer comprises at least a substance selected from the group consisting of polyoxyethylene-20-sorbitan monooleate and poly(ethylene oxide)-poly(propylene oxide)-poly(ethylene oxide) tri-block copolymer.

5. The method of claim 4, wherein said enteric-coated tablet further comprises a coating material selected from one or more of poly(methacrylic acid)-poly(methyl methacrylate) copolymer, hydroxypropyl methylcellulose phthalate or cellulose acetate phthalate.

6. A method of preventing and/or treating anemia and/or hypoxic conditions comprising orally administering an enteric-coated tablet to a subject in need thereof, wherein said enteric-coated tablet is configured to deliver the hemoglobin-based oxygen carrier in a controlled release manner to a target site along the intestinal tract of the subject, wherein said delivering to the target site along the intestinal tract is pH-dependent, and wherein said enteric-coated tablet comprises a lyophilized form of the hemoglobin based oxygen carrier a cryoprotectant, a tablet forming excipient, and one or more stabilizer and intestinal absorption enhancer, wherein said one or more stabilizer and intestinal absorption enhancer comprises at least a substance selected from the group consisting of polyoxyethylene-20-sorbitan monooleate and poly(ethylene oxide)-poly(propylene oxide)-poly(ethylene oxide) tri-block copolymer.

7. A method of preparing an enteric-coated capsule comprising:
   a) adding cryoprotectants, intestinal absorption enhancers and other stabilizers into a hemoglobin-based oxygen carrier-containing solution to form a mixture for preserving the structure of protein during lyophilization;
   b) lyophilizing the mixture obtained in (a) to form lyophilized hemoglobin molecule;

c) encapsulating a plurality of the lyophilized hemoglobin molecule into an enteric-coat to form said enteric-coated capsule,
  wherein said enteric-coated capsule is configured to deliver the hemoglobin-based oxygen carrier in a controlled release manner to a target site along the intestinal tract of a subject, and wherein said delivering to the target site along the intestinal tract is pH-dependent, and
  wherein said intestinal absorption enhancer comprises at least a substance selected from the group consisting of polyoxyethylene-20-sorbitan monooleate and poly(ethylene oxide)-poly(propylene oxide)-poly(ethylene oxide) tri-block copolymer.

8. The method claim 7, wherein said cryoprotectants are one or more of glucose, sucrose and/or trehalose.

9. The method of claim 7, wherein the other stabilizers comprise vitamin C or N-acetyl cysteine (NAC).

10. A method of preparing an enteric-coated tablet comprising:
  adding cryoprotectants, intestinal absorption enhancers and other stabilizers into a hemoglobin-based oxygen carrier-containing solution to form a mixture for preserving the structure of protein during lyophilization;
  b) lyophilizing the mixture obtained in (a) to form lyophilized hemoglobin molecule;
  c) mixing a tablet forming excipient with the lyophilized hemoglobin molecule obtained in (b) to form a thoroughly mixed powders for enabling a sustained release of the hemoglobin-based oxygen carrier into said subject's body when being orally administered to said subject;
  d) loading the thoroughly mixed powders to a machine or press to form a core tablet;
  e) film coating the core tablet by an enteric coating material to form said enteric-coated tablet,
    wherein said enteric-coated tablet is configured to deliver the hemoglobin-based oxygen carrier in a controlled release manner to a target site along the intestinal tract of a subject, and wherein said delivering to the target site along the intestinal tract is pH-dependent, and
    wherein said intestinal absorption enhancer comprises at least a substance selected from the group consisting of polyoxyethylene-20-sorbitan monooleate and poly(ethylene oxide)-poly(propylene oxide)-poly(ethylene oxide) tri-block copolymer.

11. The method of claim 10, wherein said tablet forming excipient comprises lactose monohydrate, polyvinylpyrrolidone, magnesium stearate, microcrystalline cellulose, anhydrous dibasic calcium phosphate, ethylcellulose, cellulose esters, and poly(methacrylates).

12. The method of claim 10, wherein said enteric coating material comprises poly(methacrylic acid)-poly(methyl methacrylate) copolymer, hydroxypropyl, and methylcellulose phthalate and cellulose acetate phthalate.

13. The method claim 10, wherein said cryoprotectants are one or more of glucose, sucrose and/or trehalose.

14. The method of claim 10, wherein the other stabilizers comprise vitamin C or N-acetyl cysteine (NAC).

15. The method of claim 4, wherein said hemoglobin-based oxygen carrier comprises one or more of purified hemoglobin, cross-linked hemoglobin, non-polymeric tetrameric hemoglobin, polymeric hemoglobin, or conjugated hemoglobin.

16. The method of claim 6, wherein said enteric-coated tablet further comprises a coating material selected from one or more of poly(methacrylic acid)-poly(methyl methacrylate) copolymer, hydroxypropyl methylcellulose phthalate or cellulose acetate phthalate.

17. The method of claim 3, wherein said hemoglobin-based oxygen carrier comprises one or more of purified hemoglobin, cross-linked hemoglobin, non-polymeric tetrameric hemoglobin, polymeric hemoglobin, or conjugated hemoglobin.

18. The method of claim 6, wherein said hemoglobin-based oxygen carrier comprises one or more of purified hemoglobin, cross-linked hemoglobin, non-polymeric tetrameric hemoglobin, polymeric hemoglobin, or conjugated hemoglobin.

19. The method of claim 1, wherein said polyoxyethylene-20-sorbitan monooleate is in a concentration of 3 mM and said poly(ethylene oxide)-poly(propylene oxide)-poly(ethylene oxide) tri-block copolymer is in a concentration of 0.2% w/v.

20. The method of claim 3, wherein said polyoxyethylene-20-sorbitan monooleate is in a concentration of 3 mM and said poly(ethylene oxide)-poly(propylene oxide)-poly(ethylene oxide) tri-block copolymer is in a concentration of 0.2% w/v.

21. The method of claim 4, wherein said polyoxyethylene-20-sorbitan monooleate is in a concentration of 3 mM and said poly(ethylene oxide)-poly(propylene oxide)-poly(ethylene oxide) tri-block copolymer is in a concentration of 0.2% w/v.

22. The method of claim 6, wherein said polyoxyethylene-20-sorbitan monooleate is in a concentration of 3 mM and said poly(ethylene oxide)-poly(propylene oxide)-poly(ethylene oxide) tri-block copolymer is in a concentration of 0.2% w/v.

23. The method of claim 7, wherein said polyoxyethylene-20-sorbitan monooleate is in a concentration of 3 mM and said poly(ethylene oxide)-poly(propylene oxide)-poly(ethylene oxide) tri-block copolymer is in a concentration of 0.2% w/v.

24. The method of claim 10, wherein said polyoxyethylene-20-sorbitan monooleate is in a concentration of 3 mM and said poly(ethylene oxide)-poly(propylene oxide)-poly(ethylene oxide) tri-block copolymer is in a concentration of 0.2% w/v.

* * * * *